US010552940B2

(12) United States Patent
Yamazaki et al.

(10) Patent No.: US 10,552,940 B2
(45) Date of Patent: Feb. 4, 2020

(54) MEDICAL IMAGE DIAGNOSTIC APPARATUS FOR ENLARGING AND RECONSTRUCTIVE IMAGE PORTIONS

(71) Applicant: Toshiba Medical Systems Corporation, Otawara-shi (JP)

(72) Inventors: Masahiko Yamazaki, Nasushiobara (JP); Koichi Sato, Otawara (JP); Takashi Kurihara, Otawara (JP); Yuki Kato, Otawara (JP); Takahito Watanabe, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 375 days.

(21) Appl. No.: 14/738,207

(22) Filed: Jun. 12, 2015

(65) Prior Publication Data

US 2015/0278993 A1 Oct. 1, 2015

Related U.S. Application Data

(63) Continuation of application No. PCT/JP2013/083445, filed on Dec. 13, 2013.

(30) Foreign Application Priority Data

Dec. 13, 2012 (JP) .................. 2012-272162

(51) Int. Cl.
*G06T 3/40* (2006.01)
*A61B 6/03* (2006.01)
(Continued)

(52) U.S. Cl.
CPC ............... *G06T 3/40* (2013.01); *A61B 6/032* (2013.01); *A61B 6/463* (2013.01); *A61B 8/14* (2013.01);
(Continued)

(58) Field of Classification Search
None
See application file for complete search history.

(56) References Cited

U.S. PATENT DOCUMENTS 8,089,527 B2 * 1/2012 Tomita ................... H04N 5/232
348/222.1
2004/0136606 A1 * 7/2004 Shinbata ................ G06T 5/009
382/274
(Continued)

FOREIGN PATENT DOCUMENTS

| CN | 103456002 A | 12/2013 |
| JP | 2006-305204 A | 11/2006 |
| JP | 2007-195970 A | 8/2007 |

OTHER PUBLICATIONS

International Search Report dated Feb. 4, 2014 in PCT/JP2013/083445.
(Continued)

*Primary Examiner* — Hilina K Demeter
(74) *Attorney, Agent, or Firm* — Oblon, McClelland, Maier & Neustadt, L.L.P.

(57) ABSTRACT

A medical image diagnostic apparatus includes an acquisition circuitry configured to acquire data concerning the interior of an object, a reconstruction circuitry configured to reconstruct the first image concerning the object based on the acquired data, a display, and an enlargement reconstruction circuitry configured to enlarge/reconstruct the second image corresponding to the set enlargement reconstruction range based on a portion of the acquired data, with the second image being displayed in a display area of the display in place of a portion of the first image under the control of the display control circuitry.

13 Claims, 4 Drawing Sheets

(51) Int. Cl.
  *A61B 6/00* (2006.01)
  *A61B 8/14* (2006.01)
  *A61B 8/00* (2006.01)
  *G06T 7/00* (2017.01)
  *A61B 5/055* (2006.01)

(52) U.S. Cl.
  CPC ............ *A61B 8/463* (2013.01); *G06T 7/0012* (2013.01); *A61B 5/055* (2013.01); *A61B 2576/00* (2013.01); *G06T 2207/10081* (2013.01); *G06T 2207/10088* (2013.01); *G06T 2207/10116* (2013.01)

(56) References Cited

U.S. PATENT DOCUMENTS

| | | | | |
|---|---|---|---|---|
| 2004/0190674 | A1* | 9/2004 | Tsukagoshi | A61B 6/032 378/4 |
| 2005/0063611 | A1* | 3/2005 | Toki | A61B 6/032 382/299 |
| 2006/0104412 | A1* | 5/2006 | Kawanabe | A61B 6/032 378/20 |
| 2007/0211845 | A1* | 9/2007 | Nishide | A61B 6/04 378/4 |
| 2007/0237286 | A1* | 10/2007 | Imai | A61B 6/032 378/4 |
| 2007/0237295 | A1 | 10/2007 | Gundel | |
| 2007/0258558 | A1* | 11/2007 | Nishide | A61B 6/032 378/8 |
| 2008/0019474 | A1* | 1/2008 | Nakanishi | A61B 6/032 378/9 |
| 2009/0066730 | A1* | 3/2009 | Mikawa | G06T 3/40 345/661 |
| 2010/0034443 | A1* | 2/2010 | Inoue | A61B 1/04 382/128 |
| 2011/0069875 | A1* | 3/2011 | Goto | A61B 6/032 382/131 |
| 2011/0305382 | A1* | 12/2011 | Takahashi | A61B 6/5211 382/132 |
| 2012/0121157 | A1* | 5/2012 | Irie | A61B 6/032 382/131 |
| 2013/0113802 | A1* | 5/2013 | Weersink | G06T 15/20 345/427 |
| 2013/0322716 | A1* | 12/2013 | Wollenweber | A61B 6/037 382/131 |
| 2014/0197835 | A1* | 7/2014 | Kamada | G01R 33/4824 324/309 |
| 2014/0198892 | A1* | 7/2014 | Yamakawa | A61B 6/032 378/4 |
| 2015/0235363 | A1* | 8/2015 | Bar-Shalev | A61B 6/032 382/131 |
| 2016/0128648 | A1* | 5/2016 | Miyazawa | A61B 6/025 378/21 |
| 2016/0128649 | A1* | 5/2016 | Miyazawa | A61B 6/025 378/21 |
| 2016/0331341 | A1* | 11/2016 | Brendel | A61B 6/032 |

OTHER PUBLICATIONS

International Preliminary Report on Patentability and Written Opinion dated Jun. 25, 2015 in PCT/JP2013/083445.
Office Action dated Mar. 3, 2017, in Chinese Patent Application No. 201380064697.2.

* cited by examiner

MEDICAL IMAGE DIAGNOSTIC APPARATUS FOR ENLARGING AND RECONSTRUCTIVE IMAGE PORTIONS

CROSS-REFERENCE TO RELATED APPLICATIONS

This application is a Continuation Application of PCT Application No. PCT/JP2013/0834445, filed Dec. 13, 2013 and based upon and claims the benefit of priority from the Japanese Patent Application No. 2012-272162, filed Dec. 13, 2012, the entire contents of all of which are incorporated herein by reference.

FIELD

Embodiments described herein relate generally to a medical image diagnostic apparatus and a medical image processing apparatus.

BACKGROUND

In general, in the medical field, an object is diagnosed by using the medical images obtained by a medical image diagnostic apparatus. Such a medical image diagnostic technique has become indispensable to current medical care, and a further improvement in diagnostic performance is desired.

Under the circumstances, for example, it is known that an X-ray computed tomography apparatus (to be written as an X-ray CT apparatus hereinafter) executes enlargement reconstruction (zooming-reconstruction) to improve the diagnostic performance. According to this enlargement reconstruction, a high-resolution image (an image with a high spatial resolution) is reconstructed upon limiting a reconstruction range to a portion of a scan range. Executing such enlargement reconstruction (zooming-reconstruction) makes it possible to obtain a high-resolution image corresponding to a reconstruction range, thereby improving the diagnostic performance.

When executing enlargement reconstruction in an X-ray CT apparatus, the operator must check the image (CT image) obtained by the X-ray CT apparatus, activate a function for reconstructing the image again (for example, a reconstruction retry function), and select projection data (raw data) necessary for the reconstruction. In addition, the operator must select an area as an enlargement reconstruction target (reconstruction range). With this operation, the apparatus executes enlargement reconstruction for the reconstruction range selected by the operator based on the projection data selected by the operator.

Note that the operator selects a reconstruction range by designating, for example, an enlargement ratio on an image, an enlargement center, and a reconstruction pitch representing the intervals between images in the slice direction.

As described above, when executing enlargement reconstruction, the operator needs to perform a plurality of operations. This is cumbersome for the operator.

In contrast to this, there is available a function of simply zooming (enlarging) (to be simply referred to as a zoom function hereinafter), for example, a medical image on a display screen. Using this zoom function makes it possible to easily change the enlargement position and the enlargement ratio (magnification) by using a mouse or the like. That is, the operator is only required to perform operations simpler than those required to perform the above enlargement reconstruction.

However, since a medical image is reconstructed at a low enlargement ratio by using the zoom function, even if the enlargement ratio is changed, the roughness of the medical image remains the same as that before the enlargement of the image. That is, the medical image enlarged by the zoom function is lower in diagnostic performance than the image for which the above enlargement reconstruction has been executed. In order to obtain high diagnostic performance, therefore, it is preferable to execute enlargement reconstruction.

SUMMARY OF INVENTION

The technical problem to be solved by the present invention is to provide a medical image diagnostic apparatus and a medical image processing apparatus which can execute enlargement reconstruction for a medical image without performing cumbersome operations.

DETAILED DESCRIPTION

A medical image diagnostic apparatus according to an embodiment includes: an acquisition circuitry configured to acquire data concerning an interior of an object; a reconstruction circuitry configured to reconstruct a first image concerning the object based on the acquired data; a display; a display control circuitry configured to display the reconstructed first image in a display area of the display circuitry and enlarge/display a portion of the first image in the display area in accordance with an enlarging/display operation by an operator; a range setting circuitry configured to set, as an enlargement reconstruction range, a portion of the enlarged/displayed first image; and an enlargement reconstruction circuitry configured to enlarge/reconstruct a second image corresponding to the set enlargement reconstruction range based on some of the acquired data with the second image being displayed in a display area of the display circuitry in place of a portion of the first image under the control of the display control circuitry.

An embodiment will be described below with reference to the accompanying drawings.

A medical image diagnostic apparatus according to this embodiment includes, for example, an X-ray computed tomography apparatus (X-ray CT apparatus), a magnetic resonance imaging apparatus (MRI apparatus), an X-ray diagnostic apparatus, and an ultrasonic diagnostic apparatus. The following description exemplifies an X-ray CT apparatus as a medical image diagnostic apparatus according to the embodiment.

Figure 1:
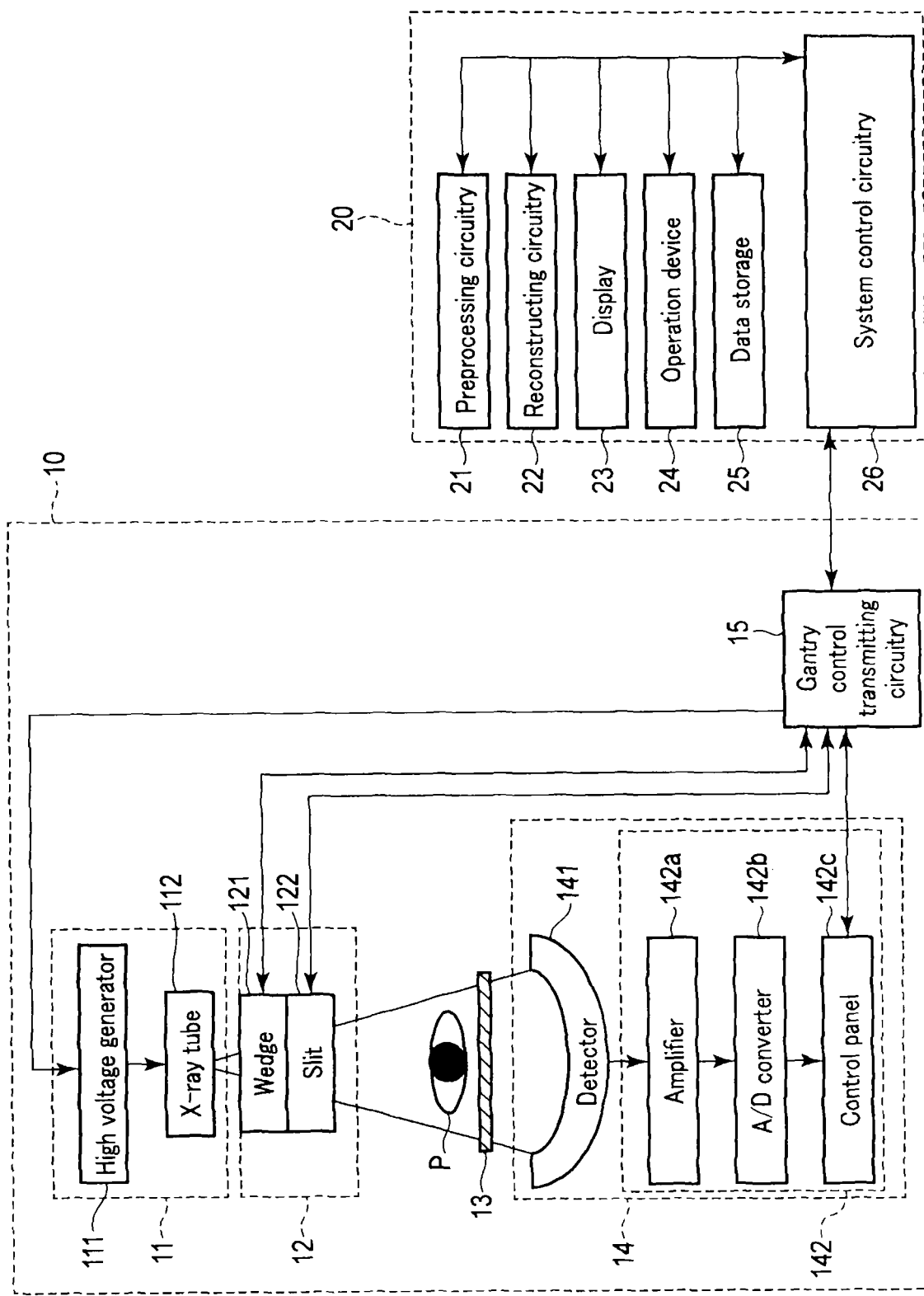
FIG. 1 is a block diagram showing the arrangement of an X-ray CT apparatus according to an embodiment.

FIG. 1 shows the arrangement of an X-ray CT apparatus according to this embodiment. As shown in FIG. 1, the X-ray CT apparatus includes a gantry 10 and a console 20.

The gantry 10 includes an X-ray system 11, an optical system 12, a couch top (bed) 13, a detection system 14, and a gantry control transmission circuitry 15.

The X-ray system 11 includes a high voltage generator 111 and an X-ray tube 112. The high voltage generator 111 applies a high voltage to the X-ray tube 112 under the control of the gantry control transmission circuitry 15, and supplies a filament current to the X-ray tube 112 under the control of the gantry control transmission circuitry 15.

The X-ray tube 112 generates X-rays to be applied to an object P upon receiving a high voltage and a filament current from the high voltage generator 111.

The optical system 12 includes a wedge (filter) 121 which cuts soft X-rays of X-rays generated from the X-ray tube 112 and adjusts the intensity distribution of the X-rays and a slit 122 which opens and closes in accordance with a slice thickness at the time of a scan. The optical system 12 described above forms a fan beam with an optimized exposure dose and irradiates the object P with X-rays.

In this case, the gantry 10 is equipped with an annular or disk-like rotating frame (not shown). The rotating frame supports the X-ray tube 112 and a detector 141 (to be described later) so as to allow them to rotate about the central axis (rotation axis) of the rotating frame. An FOV (field of view) is set in the opening of the rotating frame. The couch top 13 is positioned in the opening portion of the rotating frame. The object P is placed on the couch top 13. The couch top 13 is moved such that an imaging region of the object P placed on the couch top 13 is included in the FOV. The rotating frame is connected to a rotating frame driving circuitry (not shown), and rotates about the rotation axis (the body axis of the object P) at a predetermined angular velocity upon receiving a driving signal from the rotating frame driving circuitry. The rotating frame driving circuitry rotates the rotating frame about the rotation axis at a predetermined angular velocity under the control of the gantry control transmission circuitry 15.

The detection system 14 includes the detector 141 and a DAS (data acquisition system) 142.

The detector 141 detects the X-rays generated from the X-ray tube 112. The detector 141 is equipped with a plurality of detection elements arrayed two-dimensionally. For example, the plurality of detection elements are arrayed along an arc centered on the rotation axis of the above rotating frame. The arraying direction of the detection elements along the arc is called a channel direction. The plurality of detection elements arrayed along the channel direction are called a detection element array. A plurality of detection element arrays are arrayed along a column direction along the rotation axis of the rotating frame. Each detection element detects the X-rays generated from the X-ray tube 112 and generates an electrical signal (current signal) corresponding to the intensity of the detected X-rays. The generated electrical signal is supplied to the data acquisition system 142.

The data acquisition system 142 includes an amplifier 142a, an A/D converter 142b, and a control panel 142c. The data acquisition system 142 reads out electrical signals via the detector 141 and acquires the readout electrical signals for each view in an integral mode under the gantry control transmission circuitry 15 via the control panel 142c. More specifically, the data acquisition system 142 generates an integral signal by integrating electrical signals for each detection element for each of a plurality of views in the integral mode. The data acquisition system 142 amplifies the acquired analog electrical signals (integral signals) by using the amplifier 142a, and converts the signals into digital data by using the A/D converter 142b. This digital data is called raw data. The raw data is supplied (transmitted) to the console 20 via the noncontact type gantry control transmission circuitry 15.

The gantry control transmission circuitry 15 controls the high voltage generator 111, the wedge 121, the slit 122, the control panel 142c, and the like to execute X-ray CT imaging.

The console 20 includes a preprocessing circuitry 21, a reconstruction circuitry 22, a display 23, an operation a circuitry 24, a data storage 25, and a system control circuitry 26.

The preprocessing circuitry 21 executes preprocessing such as logarithmic conversion and sensitivity correction for the raw data supplied from the data acquisition system 142 via the gantry control transmission circuitry 15. The data for which the preprocessing has been executed is called projection data.

The reconstruction circuitry 22 reconstructs an image (first image) concerning an overall reconstruction range (to be simply referred to as a reconstruction range hereinafter) associated with the object P based on the data of the inside of the object P (projection data) acquired from the object P. The display 23 displays the image reconstructed by the reconstruction circuitry 22 in this manner. Note that the reconstruction circuitry 22 executes reconstruction processing based on, for example, the reconstruction function (reconstruction algorithm) predetermined by the operator.

In addition, the reconstruction circuitry 22 decides an area of the image which is enlarged in accordance with an operation by the operator with respect to the image displayed by the display 23 as a range as an enlargement reconstruction target (to be written as an enlargement reconstruction range hereinafter). The reconstruction circuitry 22 executes enlargement reconstruction processing based on some of data (projection data) of the interior of the object P described above. With this processing, the reconstruction circuitry 22 reconstructs a high-resolution image (second image) corresponding to the decided enlargement reconstruction range.

The display 23 displays various types of information such as the image reconstructed by the reconstruction circuitry 22 on a display device. As the display device, for example, a CRT display, liquid crystal display, organic EL display, or plasma display can be used as needed.

The operation circuitry 24 accepts various types of commands and information inputs from the user via an input device. As the input device, a keyboard, mouse, switches, and the like can be used. The operator can perform, via the operation circuitry 24, an operation to enlarge a partial area of the image displayed by the display 23 in the above manner.

The data storage 25 stores the above raw data and various types of data such as projection data and images. In addition, the data storage 25 stores control programs for the X-ray CT apparatus according to this embodiment.

The system control circuitry 26 functions as the main circuitry of the X-ray CT apparatus. More specifically, the system control circuitry 26 reads out control programs stored in the data storage 25 and loads the programs into the memory. The system control circuitry 26 controls the respective circuitry in the X-ray CT apparatus in accordance with the loaded control programs.

Figure 2:
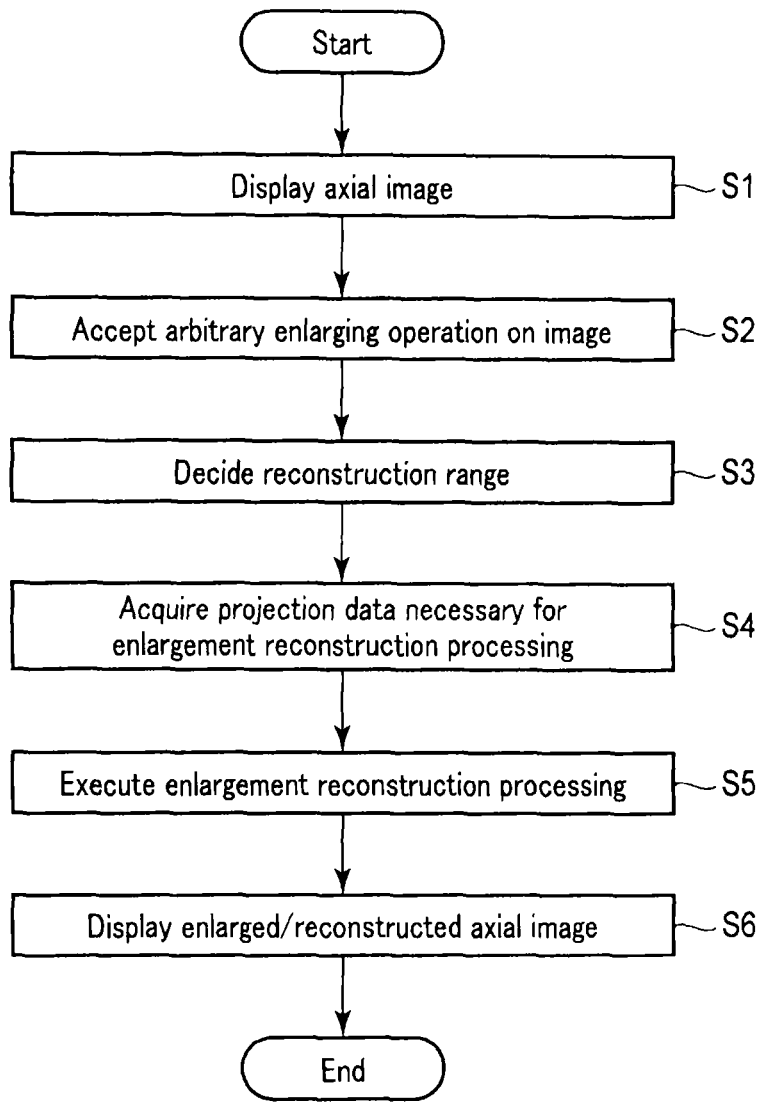
FIG. 2 is a flowchart showing a processing procedure in the X-ray CT apparatus according to this embodiment.

A processing procedure in the X-ray CT apparatus according to this embodiment will be described next with reference to the flowchart of FIG. 2. The following will mainly describe processing to be performed when the display 23 displays the image (CT image) reconstructed by the reconstruction circuitry 22 included in the console 20 of the X-ray CT apparatus, and enlargement reconstruction processing is then executed for a partial area (target region) of the image.

First of all, the display 23 displays the image reconstructed by the reconstruction circuitry 22 (to be written as the target image hereinafter) under the display control of the system control circuitry 26 (step S1). The target image displayed by the display 23 includes, for example, an axial image concerning the object P. An axial image is an image on a plane (axial plane) perpendicular to the body axis of the object P. Although an axial image will be mainly described below, this embodiment can also be applied to an MPR (Multi Planar Reconstruction) image on a predetermined slice of volume data, a three-dimensional image based on the volume data, and the like.

In this case, the operator can perform an operation (to be referred to as an enlarging operation hereinafter) to enlarge a partial area of a target image (first image) displayed by the display 23. This enlarging operation is performed by using an input device such as a keyboard, a mouse, and switches. An area of a target image to which the operator performs an enlarging operation is called an enlargement target area hereinafter.

When the operator has performed an enlarging operation (an arbitrary enlarging operation on a target image), the operation circuitry 24 accepts the enlarging operation by the operator (step S2). When the operation circuitry 24 accepts the enlarging operation, an image processing circuitry in the display 23 performs enlargement processing for a portion of the first image, i.e., an enlargement target area of the target image which corresponds to the enlarging operation. With this operation, the enlarged target image (enlarged first image) is generated and displayed by the display 23.

Processing from step S3 is executed in the background of the display operation of the target image with the above enlargement target area being enlarged.

In this case, the reconstruction circuitry 22 decides the portion of the target image (i.e., the enlargement target area) which has been enlarged in accordance with the enlarging operation accepted by the operation circuitry 24 as an enlargement reconstruction range (a range as an enlargement target) (step S3).

The reconstruction circuitry 22 then acquires, from the data storage 25, some of projection data which is required to execute enlargement processing for the area decided as the enlargement reconstruction range (step S4). Note that the projection data required to execute enlargement reconstruction processing for the reconstruction range includes the projection data used for reconstruction of the above target image.

The reconstruction circuitry 22 executes enlargement reconstruction processing for the area decided as the enlargement reconstruction range in step S3 based on the acquired projection data (step S5). With this processing, the reconstruction circuitry 22 reconstructs an image (to be written as an enlarged reconstructed image or second image hereinafter) corresponding to the area decided as the enlargement reconstruction range. The enlarged reconstructed image in this case is higher in resolution than the image (i.e., the enlarged first image) before the execution of the enlargement reconstruction processing. Although the reconstruction function used to execute this enlargement reconstruction processing may be that used to reconstruct the target image, it is possible to use a reconstruction function which can reconstruct an image with a higher resolution than that used to reconstruct the target image. This can further improve the diagnostic performance of the enlarged reconstructed image.

When the reconstruction circuitry 22 has executed enlargement reconstruction processing in this manner, the display 23 displays an enlarged reconstructed image (axial image) (step S6). More specifically, the display 23 displays the enlarged reconstructed image in place of the target image displayed with its enlargement target area being simply enlarged.

According to this embodiment, with regard to image switching display, the display 23 selectively displays the first image concerning an overall object, the enlarged first image generated by processing the first image, and the second image concerning an enlargement reconstruction range corresponding to a portion of the first image based on some of projection data.

In this embodiment, when the operator simply performs an enlarging operation for a displayed target image, enlargement reconstruction processing is automatically executed to display an enlarged reconstructed image. This enables the operator to check a high-resolution image of a region (area) desired by the operator.

Note that it is preferable to make settings in advance to execute processing from step S3 described above when, for example, the enlargement ratio of a target image (its enlargement target area) corresponding to an enlarging operation by the operator becomes equal to or more than a predetermined value (i.e., equal to or more than a certain value). This makes it unnecessary for the operator to perform a specific operation for the execution of enlargement reconstruction, and hence can quickly execute enlargement reconstruction without waiting for any operation by the operator.

In addition, according to the above description, enlargement reconstruction processing is executed for only the enlargement target area of a displayed image. However, it is possible to execute enlargement reconstruction processing for an area 102 including an enlargement target area 101 like that shown in FIG. 3 and its peripheral area by, for example, deciding, as an enlargement reconstruction range, an enlargement target area and a peripheral area of the enlargement target area in the processing in step S3. This allows the operator to check a high-resolution image without waiting for the execution of enlargement reconstruction processing even if the operator shifts his/her viewpoint from the enlargement target area 101 to an area 103 shown in FIG. 3.

If, for example, the enlargement target area 101 decided as an enlargement reconstruction range is a circular area, the area 102 including the enlargement target area 101 and its peripheral area can be a circular area (range) having the same center as that of the enlargement target area 101 and a radius twice as that of the enlargement target area 101. For example, the operator can change the area 102 decided as this enlargement reconstruction range, as needed, based on a range or the like which he/she can check by single operation.

Figure 3:
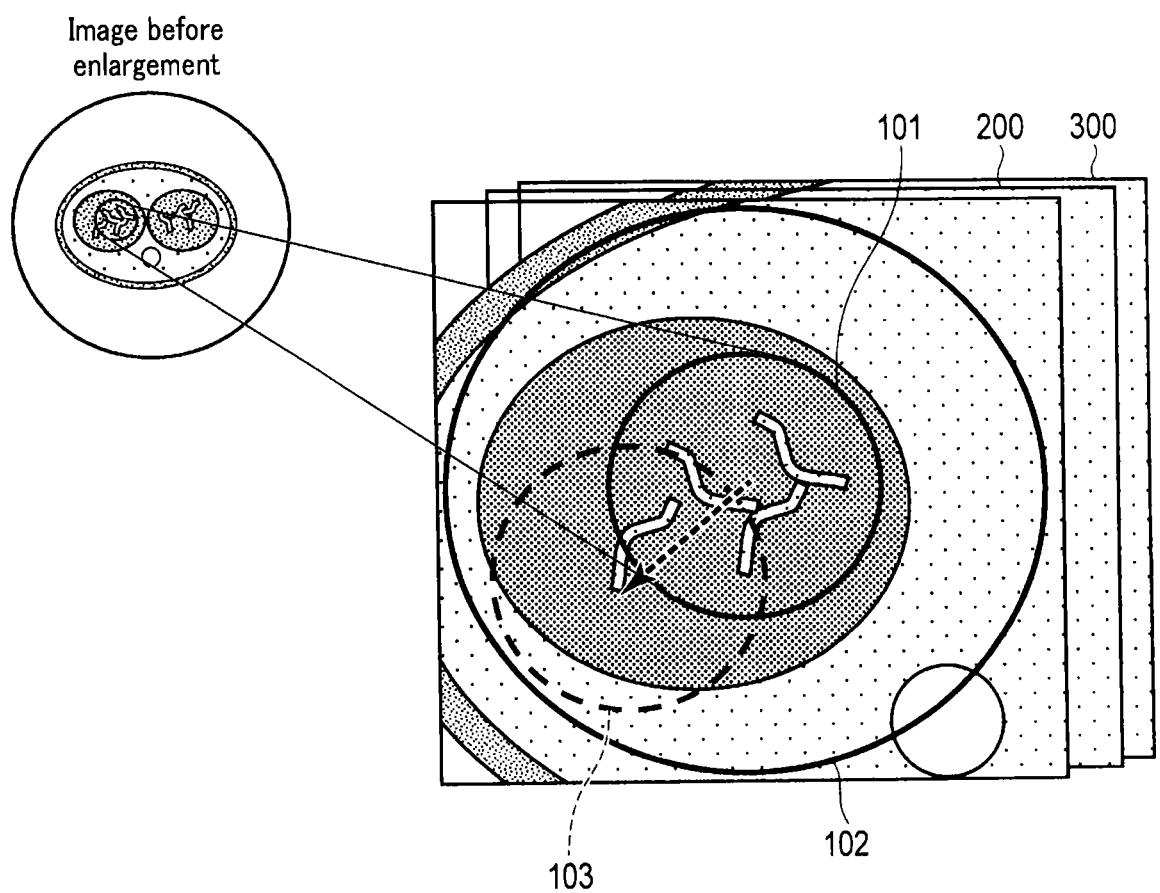
FIG. 3 is a view for explaining an area including an enlargement target area decided as a reconstruction range and a peripheral area.

In addition, it is possible to execute enlargement reconstruction processing for not only a displayed target image but also a plurality of images (third images) differing in slice position from the target image, i.e., areas such as images 200 and 300 shown in FIG. 3. In this case, enlargement reconstruction is automatically executed even in the slice direction by, for example, further deciding, as enlargement reconstruction ranges, the areas of the images 200 and 300 corresponding to enlargement target areas (and their peripheral areas) in the processing in step S3. This allows the operator to check high-resolution images even when making a check in the slice direction, without waiting for the execution of enlargement reconstruction processing for each operation.

Note that, as described above, when the areas of images differing in slice position from a target image are decided as enlargement reconstruction ranges, enlargement reconstruction processing is executed for the areas of the images in ascending order of distance from the slice position of the target image. This allows the operator to check high-resolution images without waiting for the execution of reconstruction in ascending order of distance from a region displayed on a current image (target image).

Assume that a reconstruction pitch at which enlargement reconstruction processing is executed for the areas of images differing in slice position from a target image is automatically decided from the reconstruction pitch set for the target image (axial image) and the enlargement ratio of the enlargement target area of the target image. More specifically, if the enlargement ratio of the enlargement target area of a target image is two, the reconstruction pitch at which enlargement reconstruction processing is executed for the areas of images differing in slice position from the target image is automatically decided to be, for example, ½ that set for the target image.

Figure 4:
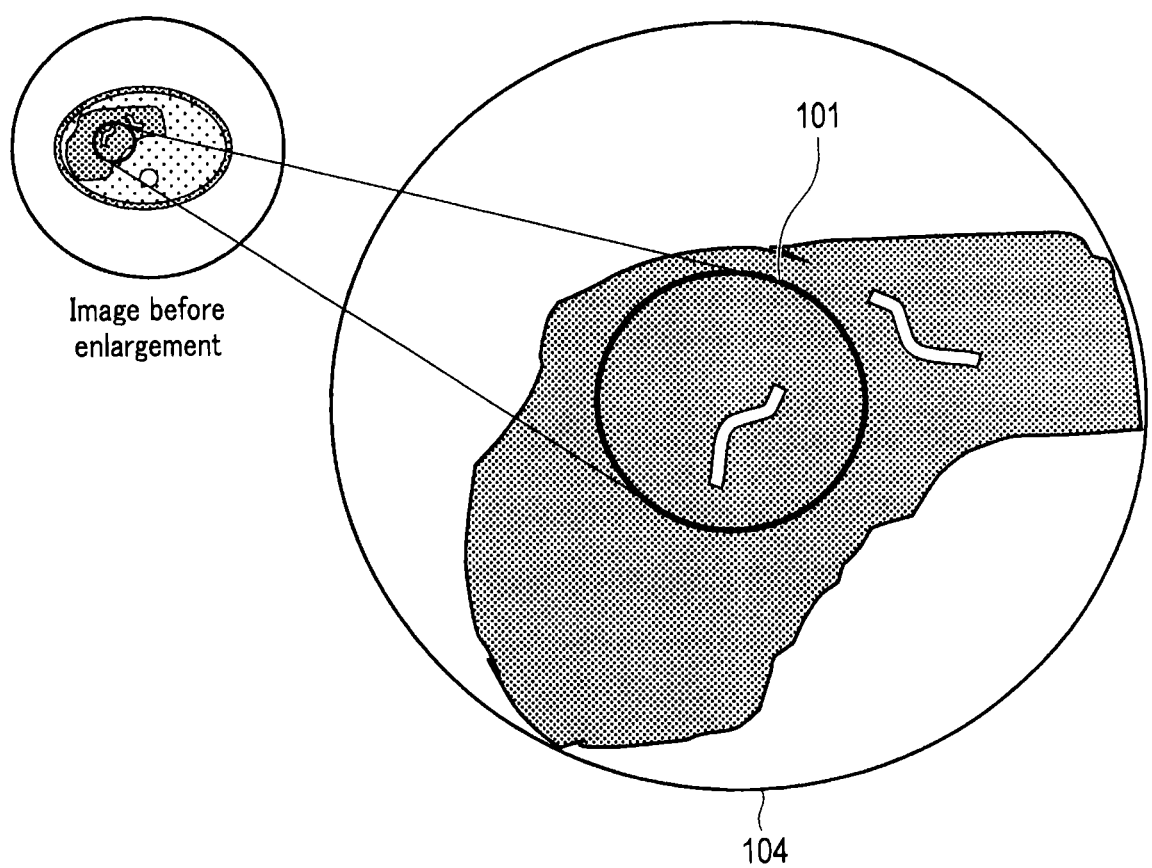
FIG. 4 is a view for explaining an area including a region to be displayed in an enlargement target area decided as a reconstruction range.

Referring to FIG. 3, enlargement reconstruction processing is executed for the area 102 including the enlargement target area 101 set as needed and its peripheral area. However, as shown in FIG. 4, it is possible to decide, as an enlargement reconstruction range, for example, an area 104 including a tissue (e.g., an organ) in the object P displayed in the area of the target image (i.e., the enlargement target area) enlarged in accordance with an operation by the operator and to execute enlargement reconstruction processing for the area 104. In this case, for example, whether a region displayed in an enlargement target area exists in a given organ may be discriminated from, for example, a boundary with respect to the CT values of a target image (a CT image in this case), and an area including the organ may be decided as the area 104. This makes it possible to check a high-resolution image without waiting for the execution of enlargement reconstruction processing even if the viewpoint is shifted in the area of the organ displayed in an enlargement target area. When executing enlargement reconstruction processing for an area of an image differing in slice position from a target image, as described above, a similar area of the image can be decided as an enlargement reconstruction range.

As described above, this embodiment is configured to decide, as an enlargement reconstruction range, an area of a displayed image which is enlarged by an operation by the operator with respect to the displayed image, reconstruct an image corresponding to the area decided as the enlargement reconstruction range based on data (projection data) of the interior of the object P, and display the reconstructed image, thereby automatically executing enlargement reconstruction (zooming-reconstruction) by only performing a simple enlarging operation. This allows the operator to check a high-resolution image without performing any cumbersome operation.

According to the above description, this embodiment is configured to execute enlargement reconstruction processing. However, it is possible to execute, for example, image filter processing instead of this enlargement reconstruction processing. More specifically, when, for example, re-displaying an image of the lung fields or the like upon applying a sharp image filter to the image, the embodiment can be configured to reconstruct an image by using a sharper function with respect to a re-displayed area in the background and display the reconstructed image in place of the displayed image. In addition, it is possible to simultaneously execute an enlarging operation by the operator with respect to a plurality of axial images in the background, thereby saving the troublesome task of performing the enlarging operation every time the image is changed to the next image.

In addition, for example, this embodiment may be configured to register an enlarging operation in advance (perform simple operation registration in advance) to allow the operator to perform the enlarging operation with a frequently used operation. This makes it possible to perform an enlarging operation with "ctrl+wheel" of a mouse which is generally used to enlarge, for example, a text or the like, thereby improving the operability.

In addition, according to this embodiment, when, for example, the enlargement ratio of a target image corresponding to an enlarging operation by the operator becomes equal to or more than a predetermined value, an enlargement reconstruction range is decided, and enlargement reconstruction processing is executed. However, for example, as described above, it is possible to execute enlargement reconstruction processing by a simple operation registered in advance (for example, double clicking on the left button of the mouse or selection from a displayed menu with the right button of the mouse). Note that it is also possible to improve the operability by registering other operations in the form of, for example, shortcut keys or mouse gestures.

Although an X-ray CT apparatus has mainly been described above as an example of a medical image diagnostic apparatus according to this embodiment, modalities such as an X-ray CT apparatus, MRI apparatus, X-ray diagnostic apparatus, and ultrasonic diagnostic apparatus can be used as medical image diagnostic apparatuses according to the embodiment.

In addition, the processing described in this embodiment may be executed in a medical image processing apparatus (for example, a workstation in charge of image processing unlike the above modalities) outside a medical image diagnostic apparatus. In this case, medical images such as CT images are stored in the medical image processing apparatus in advance, and the medical image processing apparatus can execute the processing shown in FIG. 2 described above for the medical images.

Although several embodiments have been described above, they are merely examples and not intended to limit the scope of the present invention. These embodiments can be implemented in other various forms, and various omissions, replacements, and changes can be made without departing from the spirit of the present invention. The embodiments and their modifications are incorporated in the scope and sprit of the present invention, and are also incorporated in the scope of the invention and its equivalents defined in the appended claims.

The invention claimed is:
1. A medical image diagnostic apparatus, comprising:
a display; and
processing circuitry configured to
   acquire data concerning an interior of an object,
   reconstruct a first image concerning the object based on the acquired data,
   display the reconstructed first image in a display area of the display,
   enlarge a portion of the first image in the display area in accordance with an enlargement ratio set by an enlarging operation by an operator, and in response to the enlargement ratio exceeding a predetermined value,
determine, as an enlargement reconstruction range, an area of the enlarged portion of the first image displayed in the display area,
reconstruct a second image corresponding to the determined enlargement reconstruction range based on a subset of the acquired data, and
display the reconstructed second image in the display area.

2. The medical image diagnostic apparatus of claim 1, wherein the processing circuitry is further configured to determine, as the enlargement reconstruction range, the area of the first image displayed in the display area and a peripheral portion of the area of the first image.

3. The medical image diagnostic apparatus of claim 1, wherein the processing circuitry is further configured to determine, as the enlargement reconstruction range, a range including a region of the object included in the portion of the first image displayed in the display area.

4. The medical image diagnostic apparatus of claim 1, wherein the processing circuitry is further configured to determine, as the enlargement reconstruction range, a range differing in slice position from the first image and corresponding to the portion of the first image.

5. The medical image diagnostic apparatus of claim 4, wherein the processing circuitry is further configured to determine portions of a plurality of slices differing in slice position from the first image as a plurality of enlargement reconstruction ranges, and perform enlargement reconstruction of the slices in ascending order of distance from a slice of the first image.

6. The medical image diagnostic apparatus of claim 1, wherein the first image includes an MPR image on a predetermined slice of volume data and a three-dimensional image based on volume data.

7. The medical image diagnostic apparatus of claim 1, wherein the processing circuitry is further configured to display the enlarged portion of the first image, and in response to the enlargement ratio exceeding the predetermined value, display the second image instead of the enlarged portion of the first image.

8. A medical image processing apparatus, comprising:
a display;
a memory configured to store data concerning an interior of an object; and
processing circuitry configured to
reconstruct a first image concerning the object based on the data,
display the reconstructed first image in a display area of the display,
enlarge a portion of the first image in the display area in accordance with an enlargement ratio set by an enlarging operation by an operator, and
in response to the enlargement ratio exceeding a predetermined value,
determine, as an enlargement reconstruction range, an area of the enlarged portion of the first image displayed in the display area,
reconstruct a second image corresponding to the determined enlargement reconstruction range based on a subset of the acquired data, with the second image being displayed in the display area of the display in place of a portion of the first image, and
display the reconstructed second image in the display area.

9. The medical image processing apparatus of claim 8, wherein the processing circuitry is further configured to determine, as the enlargement reconstruction range, the area of the first image displayed in the display area and a peripheral portion of the area of the first image.

10. The medical image processing apparatus of claim 8, wherein the processing circuitry is further configured to determine, as the enlargement reconstruction range, a range including a region of the object included in the portion of the first image displayed in the display area.

11. The medical image processing apparatus of claim 8, wherein the processing circuitry is further configured to determine, as the enlargement reconstruction range, a range differing in slice position from the first image and corresponding to the portion of the first image.

12. The medical image diagnostic apparatus of claim 11, wherein the processing circuitry is further configured to determine portions of a plurality of slices differing in slice position from the first image as a plurality of enlargement reconstruction ranges, and perform enlargement reconstruction of the slices in ascending order of distance from a slice of the first image.

13. The medical image diagnostic apparatus of claim 8, wherein the first image includes an MPR image on a predetermined slice of volume data and a three-dimensional image based on the volume data.

* * * * *